US011219730B2

(12) United States Patent
Dellaca et al.

(10) Patent No.: US 11,219,730 B2
(45) Date of Patent: Jan. 11, 2022

(54) DEVICE FOR FACILITATING THE ADMINISTRATION OF A MEDICAMENT TO THE LUNG BY A CATHETER

(71) Applicant: CHIESI FARMACEUTICI S.P.A., Parma (IT)

(72) Inventors: Raffaele Dellaca, Parma (IT); Ilaria Milesi, Parma (IT); Emanuela Zannin, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 433 days.

(21) Appl. No.: 15/567,578

(22) PCT Filed: Apr. 27, 2016

(86) PCT No.: PCT/EP2016/059422
§ 371 (c)(1),
(2) Date: Oct. 18, 2017

(87) PCT Pub. No.: WO2016/174098
PCT Pub. Date: Nov. 3, 2016

(65) Prior Publication Data
US 2018/0104429 A1    Apr. 19, 2018

(30) Foreign Application Priority Data

Apr. 28, 2015 (WO) ................. PCT/EP2015/059251
Nov. 25, 2015 (EP) ...................................... 15196231

(51) Int. Cl.
*A61M 16/04*    (2006.01)
*A61L 31/04*    (2006.01)
(Continued)

(52) U.S. Cl.
CPC ....... *A61M 16/0497* (2013.01); *A61L 31/048* (2013.01); *A61L 31/06* (2013.01);
(Continued)

(58) Field of Classification Search
CPC .............. A61M 16/04; A61M 16/0402; A61M 16/0431; A61M 16/0463; A61M 16/0465;
(Continued)

(56) References Cited

U.S. PATENT DOCUMENTS 4,249,529 A * 2/1981 Nestor .............. A61M 16/0488
128/207.17
5,193,533 A * 3/1993 Body ................ A61M 16/0418
128/207.14
(Continued)

FOREIGN PATENT DOCUMENTS

| DE | 10 2008 015050 | 9/2009 |
|---|---|---|
| GB | 2444779 | 6/2008 |
| WO | WO 2016/109390 A1 | 7/2016 |

OTHER PUBLICATIONS

International Preliminary Report on Patentability and Written Opinion dated Nov. 9, 2017 in PCT/EP2016/059422 (submitting English translation only).
(Continued)

*Primary Examiner* — Elliot S Ruddie
(74) *Attorney, Agent, or Firm* — Oblon, McClelland, Maier & Neustadt, L.L.P.

(57) ABSTRACT

A device (100) for facilitating the positioning of a catheter for the delivery of liquid medicament to spontaneously breathing patient, including: —an elongated main body (101) shaped to follow the internal shape of the patient's upper airways, the elongated main body (101) being provided with guiding means (107) adapted to house a catheter; —a substantially ring-shaped terminal element (103) adapted to engage the internal wall of the patient's retropharynx, the substantially ring-shaped terminal element (103) being connected to the elongated main body (101) by means of at least one spoke (105), the substantially ring-shaped element (103) and the at least one spoke (105)
(Continued)

creating a chamber where the medicament can be delivered through the catheter.

16 Claims, 8 Drawing Sheets

(51) Int. Cl.
*A61L 31/06* (2006.01)
*A61L 31/14* (2006.01)
*A61L 31/16* (2006.01)

(52) U.S. Cl.
CPC .............. *A61L 31/14* (2013.01); *A61L 31/16* (2013.01); *A61M 16/0434* (2013.01); *A61M 16/0463* (2013.01); *A61M 16/0486* (2014.02); *A61M 16/0488* (2013.01); *A61M 2202/0488* (2013.01); *A61M 2209/06* (2013.01); *A61M 2240/00* (2013.01)

(58) Field of Classification Search
CPC .......... A61M 16/0475; A61M 16/0484; A61M 16/0488; A61M 16/0497; A61M 16/0816; A61M 2209/06; A61M 25/0021; A61M 25/0023; A61M 2025/0024; A61M 25/0069; A61M 25/0068; A61M 25/0074; A61M 25/0082; A61M 16/0477–0488; A61M 25/0067–0074; A61M 25/008; A61M 2025/0081; A61B 1/0008; A61B 1/00085; A61B 1/00086–00091
See application file for complete search history.

(56) References Cited

U.S. PATENT DOCUMENTS

| | | | |
|---|---|---|---|
| 5,203,320 A * | 4/1993 | Augustine | A61M 16/0488 128/200.26 |
| 5,507,279 A * | 4/1996 | Fortune | A61M 16/0472 128/200.26 |
| 6,609,520 B1 | 8/2003 | Carlsen et al. | |
| 7,533,670 B1 * | 5/2009 | Freitag | A61M 16/024 128/204.23 |
| 2008/0287888 A1 * | 11/2008 | Ravenscroft | A61M 25/0075 604/249 |
| 2010/0147311 A1 * | 6/2010 | Nierich | A61M 16/04 128/207.14 |
| 2010/0189808 A1 | 7/2010 | Gupta et al. | |
| 2013/0284181 A1 | 10/2013 | Guerra | |
| 2013/0333695 A1 * | 12/2013 | Dellaca | A61B 5/036 128/200.14 |
| 2014/0000622 A1 * | 1/2014 | Azagury | A61M 16/0434 128/207.15 |
| 2014/0014103 A1 | 1/2014 | Smaldone et al. | |
| 2015/0141942 A1 * | 5/2015 | Garrett | A61M 1/008 604/319 |
| 2015/0250966 A1 * | 9/2015 | Shabat | A61M 16/0465 128/200.26 |
| 2016/0199609 A1 | 7/2016 | Gulka et al. | |

OTHER PUBLICATIONS

International Search Report and Written Opinion for PCTPCT/EP2016/059422 dated Jul. 13, 2016.

* cited by examiner

DEVICE FOR FACILITATING THE ADMINISTRATION OF A MEDICAMENT TO THE LUNG BY A CATHETER

CROSS-REFERENCE TO RELATED APPLICATIONS

The present application is a U.S. National Stage under 35 U.S.C. § 371 of International Application No. PCT/EP2016/059422, titled "DEVICE FOR FACILITATING THE ADMINISTRATION OF A MEDICAMENT TO THE LUNG BY A CATHETER", filed on Apr. 27, 2016, which claims priority to International Application No. PCT/EP2015/059251, titled "DEVICE FOR FACILITATING THE ADMINISTRATION OF A MEDICAMENT TO THE LUNG BY A CATHETER", filed Apr. 28, 2015, and claims priority to EP Application No. 15196231.3, titled "DEVICE FOR FACILITATING THE ADMINISTRATION OF A MEDICAMENT TO THE LUNG BY A CATHETER", filed on Nov. 25, 2015, the entire contents of all of which are incorporated herein by reference.

FIELD OF TECHNOLOGY

The present invention relates to the field of instillation of medicament and particularly to a device for facilitating the administration of a liquid or aerosol medicament to the lung (e.g. a pulmonary surfactant), by a thin catheter.

BACKGROUND OF THE INVENTION

Administration of medicament in the lungs often faces with the problem of finding a right balance between the treatment efficacy and the invasiveness of the method. This is particularly true for infants (hereinafter the term neonates is used as synonymous of infants). Among other diseases, pre-term neonates may be affected by nRDS (neonatal Respiratory Distress Syndrome), a respiratory disease due to generalized lung immaturity which causes pulmonary surfactant deficiency. For many years, nRDS has been treated by administration of exogenous pulmonary surfactants as bolus through endotracheal instillation to the intubated pre-term neonates kept under mechanical ventilation at least for a very brief time. Although this treatment is very effective, as proven by the reduced mortality and improved long term quality of life, it may present some drawbacks. On one side there are the intrinsic drawbacks of the mechanical ventilation (volu/barotrauma) and to the intubation procedure which is anyway invasive and may lead to chronic lung disease (also known as bronchopulmonary dysplasia).

One the other hand the administration of a bolus may have systemic effect, such as fast variation in cerebral blood flow, due to the administration of a big amount of liquid, compared to tidal volume, into the lungs.

In view of the potential complications in intubated neonates at birth, scientific attention has been focused on different approaches of exogenous pulmonary surfactants administration of exogenous pulmonary surfactants aiming at avoiding or limiting the use of invasive mechanical ventilation.

Moreover, the new guidelines for the treatment of the preterm infants suggest avoiding the use of invasive ventilation whenever it is possible and preferring non-invasive approaches, which means that infants are no longer intubated if it is not strictly necessary and consequently they would be intubated just for the administration of the surfactant. All these modalities rely on the premise that preterm infants are mainly nose-breathers, thus all the interfaces developed for the ventilatory support, provide gas flow at the nose by means of nasal prongs, nasal cannulae, nasal masks and so on.

In particular, as a possible respiratory support, the use of non-invasive ventilation modalities such as early nasal Continuous Positive Airway Pressure (nCPAP) or High Flow Nasal Cannula (HFNC), that delivers air into the lungs through specifically designed nasal devices such as masks, prongs or tubes, has been introduced in neonatal intensive care units (NICUs).

Nasal CPAP therapy aims to support neonates, especially pre-term and low-birth weight newborns, who can breathe spontaneously but inadequately. The therapy is non-invasive, low cost, clinically effective and safe. When applied properly and promptly, nasal CPAP could minimize both the need for intubation and mechanical ventilation and promote early extubation, as well as decrease incidence of chronic lung disease. HFNC is a recent modality of ventilation that is put aside to nCPAP. HFNC consists in providing high flow of heated and humidified air by means of nasal prongs although it is still under the evaluation of the Scientific Community, it is well accepted in NICUs thanks to the facility in the management and to very promising results.

Following this orientation, in the last fifteen years great attention has also been paid to find out alternative less invasive way for pulmonary surfactant administration, possibly in combination with non-invasive ventilation supports.

For example, the use of a gastric tube placed in the trachea supported with nCPAP has been proposed in WO 2008/148469. Similar devices such as vascular catheters or nasogastric tubes were also disclosed in the art (Dargaville P A et al Arch Dis Fetal Neonatal Ed 2013, 98(2), 122-126; Aguar M et al Acta Paediatrica, ISSN 0803-5253, first published on-line on Mar. 15, 2014).

As an alternative approach, surfactant atomization was proposed in Wagner M et al Crit Care Med 2000, 28, (7), 2540-2544.

In this respect, WO2013/160129 discloses a method and system for delivering by atomization an aerosol medicament to a patient, including a thin multi lumen flexible catheter to be inserted in the retro-pharyngeal region of the patient.

The above mentioned document discloses a method and system which makes use of air/blasting technique to deliver atomized particles to the lungs, optimizing the dispensing of surfactant without invasive operations. The described solution provides several advantages including: a more gentle atomizing process, thanks to the air-blasting atomizing catheter, whose mechanical impact on the surfactant is minimal; an easier manufacturing and a more compact design of the atomizing catheter and the possibility to monitor and to synchronize to the breathing pattern of the patient without the introduction of a dedicated line for sensing the phase of breath, connections at the airway opening or a second lumen. One of the key advantages of such method and system is that it can be used during non-invasive mechanical ventilation, CPAP and spontaneous breathing.

However, in order to properly exploit the advantages of the aforementioned methods and systems, a device for facilitating the insertion and correctly positioning the catheter is required.

Preferably, said device should be able to get to its appropriate position without the need of visual inspection devices such as fiberscopes and/or other common state of the art tools such Magill forceps.

On the other hand, said device should not impede the breathing airflow and should be compatible with respiratory support systems such as nasal Continuous Positive Airway Pressure or High Flow Nasal Cannula.

In fact, the effectiveness of treatment depends on the possibility of correctly positioning the catheter.

In particular, in the case of atomization, the device should be able of positioning the tip of the atomizing catheter in a proper relative position and with a proper orientation with respect to the vocal chords. In more details, the tip of the atomizing catheter should be placed few millimeters above the vocal chords and it should be pointing towards the inlet of the trachea, to avoid the injection of the atomized drug into the esophagus or on the pharynx walls, wasting it. In addition, the device should keep the soft tissues of the pharyngeal wall away from the tip of the atomizing catheter, to allow it to atomize the medicament efficiently and not to trigger vagal reflexes.

No suitable systems are available at the state of the art. In fact current medical devices such as oro-pharyngeal cannulae, e.g Mayo cannula, and laryngeal mask only address the problem of maintaining the airways opened.

In particular, the Mayo cannula does not allow a proper positioning of the catheter and does not help in keeping such catheter in the right position relatively to the pharyngeal walls; furthermore the morphology of the cannula creates an obstacle to the passage of air, when used during ventilation modalities through the nose (e.g. nasal CPAP) or when applied to spontaneously breathing patients.

GB 2444779 discloses a laryngeal mask lung ventilation in a patient, comprising a conduit adapted to direct a liquid substance through the glottic opening, into the trachea.

Document WO 2012/032290 A1 discloses a laryngeal mask adapted for liquid drug delivery using a catheter: with such a device it is possible to correctly positioning the catheter thanks to its shape. However, since it seals around the circumference of the laryngeal inlet, said device has the drawback of completely preventing the passage of air through the nose, thus being incompatible with non-invasive modalities of ventilation commonly used on infants (e.g. nasal CPAP or HFNC) or with the use of the catheter in spontaneously breathing patients.

Objects of the Invention

It is an object of the present invention to overcome at least some of the problems associated with the prior art.

SUMMARY OF THE INVENTION

The present invention provides devices and methods as set out in the accompanying claims. According to one aspect of the present invention, we provide a device for facilitating the positioning of a catheter for the delivery of liquid medicament to spontaneously breathing patient, including: an elongated main body shaped to follow the internal shape of the patient's upper airways, the elongated main body being provided with guiding means adapted to house a catheter; a substantially ring-shaped terminal element adapted to engage the internal wall of the patient's retro-pharynx, the substantially ring-shaped terminal element being connected to the elongated main body by means of at least one spoke, the substantially ring-shaped element and the at least one spoke creating a chamber where the medicament can be delivered through the catheter, without impeding the way to the airflow through the natural airways. Preferably the substantially ring shaped element includes a toroidal element spaced apart from and connected to the elongated main body by a plurality of spokes which ensure the airflow through the natural ways.

In a preferred embodiment of the present invention the device further comprises positioning means for fixing the device to the patient. Such positioning means can include a substantially plate shaped element, which can be useful to hold the device in place.

The material of the elongated body can be selected e.g. among the following material: polyethylene (PET), polyvinyl chloride (PVC), polyurethane (PU). The ring shaped element can be of the same material or, optionally made of grade silicone.

The substantially ring-shaped element can have an elliptic shape or any substantially circular shape able to create a chamber for the delivery of the drug.

In a preferred embodiment, the ring-shaped element includes an inflatable element which provides a higher surface contact accounting for a better distribution of the forces with improved tolerability.

Alternatively the substantially ring-shaped element can be constituted by two separate portions creating a non-continuous ring adapted for reducing the interaction with the patient's retro-pharynx.

In a preferred embodiment the guiding means include a passing through hole having a preferable diameter between 0.5 mm and 3 mm, in order to allow the housing of the atomizing catheter.

In the present disclosure the term "patient" can be applied to any mammal such as a human patient and a non-human primate as well as experimental animals such as piglets and lambs, preferably to a spontaneously breathing human patient, more preferably to a spontaneously breathing pre-term neonate.

Preferably, the medicament comprises an exogenous pulmonary surfactant, e.g. selected from the group consisting of modified natural pulmonary surfactants (e.g. poractant alfa), artificial surfactants, and reconstituted surfactants.

According to a second aspect, the present invention concerns the use of the aforementioned device in combination with a catheter for the delivery of a medicament to spontaneously breathing patients.

In a third aspect of the invention, we provide a method for preventing and/or treating a respiratory distress syndrome in a spontaneously breathing patient, said method comprising the step of applying the aforementioned device in combination with a catheter for the delivery of a medicament.

In a particular embodiment, said catheter is mounted on a system for delivering by atomization a medicament in the pharyngeal region of the patient. More preferably, the method of the invention comprises applying to the patient a non-invasive ventilation modalities such as nasal Continuous Positive Airway Pressure (nCPAP) or HFNC.

In a fourth aspect of the invention, we provide a kit comprising: a) a catheter; b) the above described device for positioning and/or facilitating the introduction of the catheter into the mouth and pharynx of a patient; c) a medicament and d) container means for containing the medicament, the device and the catheter.

The method and system according to preferred embodiments of the present invention allows and facilitates the correct positioning of a catheter for the delivery of a liquid medicament (e.g. surfactant). The method and system of the present invention provides several advantages including, but not limited to, non-invasive operation in spontaneously breathing patients.

The system of the invention could be utilized for facilitating delivery of a medicament for the prevention and/or treatment of the respiratory distress syndrome (RDS) of the neonate (nRDS) and of the adult (ARDS) as well as for the prevention and/or treatment of any disease related to a surfactant-deficiency or dysfunction such as meconium aspiration syndrome, pulmonary infection (e.g. pneumonia), direct lung injury and bronchopulmonary dysplasia.

Therefore, a further aspect of the present invention is directed to the use of a pulmonary surfactant administered by means of the above described device for the prevention and/or treatment of the aforementioned disease and to a therapeutic method thereof.

BRIEF DESCRIPTION OF THE DRAWINGS

Reference will now be made, by way of example, to the accompanying drawings, in which.

DEFINITIONS

With the term "pulmonary surfactant" it is meant an exogenous pulmonary surfactant administered to the lungs that could belong to one of the following classes:
i) "modified natural" pulmonary surfactants which are lipid extracts of minced mammalian lung or lung lavage. These preparations have variable amounts of SP-B and SP-C proteins and, depending on the method of extraction, may contain non-pulmonary surfactant lipids, proteins or other components. Some of the modified natural pulmonary surfactants present on the market, like Survanta™ are spiked with synthetic components such as tripalmitin, dipalmitoylphosphatidylcholine and palmitic acid.
ii) "artificial" pulmonary surfactants which are simply mixtures of synthetic compounds, primarily phospholipids and other lipids that are formulated to mimic the lipid composition and behavior of natural pulmonary surfactant. They are devoid of pulmonary surfactant proteins;
iii) "reconstituted" pulmonary surfactants which are artificial pulmonary surfactants to which have been added pulmonary surfactant proteins/peptides isolated from animals or proteins/peptides manufactured through recombinant technology such as those described in WO 95/32992 or synthetic pulmonary surfactant protein analogues such as those described in WO 89/06657, WO 92/22315, and WO 00/47623.

The term "non-invasive ventilation" (NIV) procedure defines a ventilation modality that supports breathing without the need for intubation.

The term "prophylaxis" refers to the use for reducing the occurrence of the disease, while the term "treatment" refers to the use for palliative, curing, symptom-allievating, symptom-reducing, disease regression-inducing therapy.

The term "pre-term neonate" refers to a baby whose birth occurs earlier than 37 weeks gestational age.

DETAILED DESCRIPTION OF PREFERRED EMBODIMENTS

Figure 1:
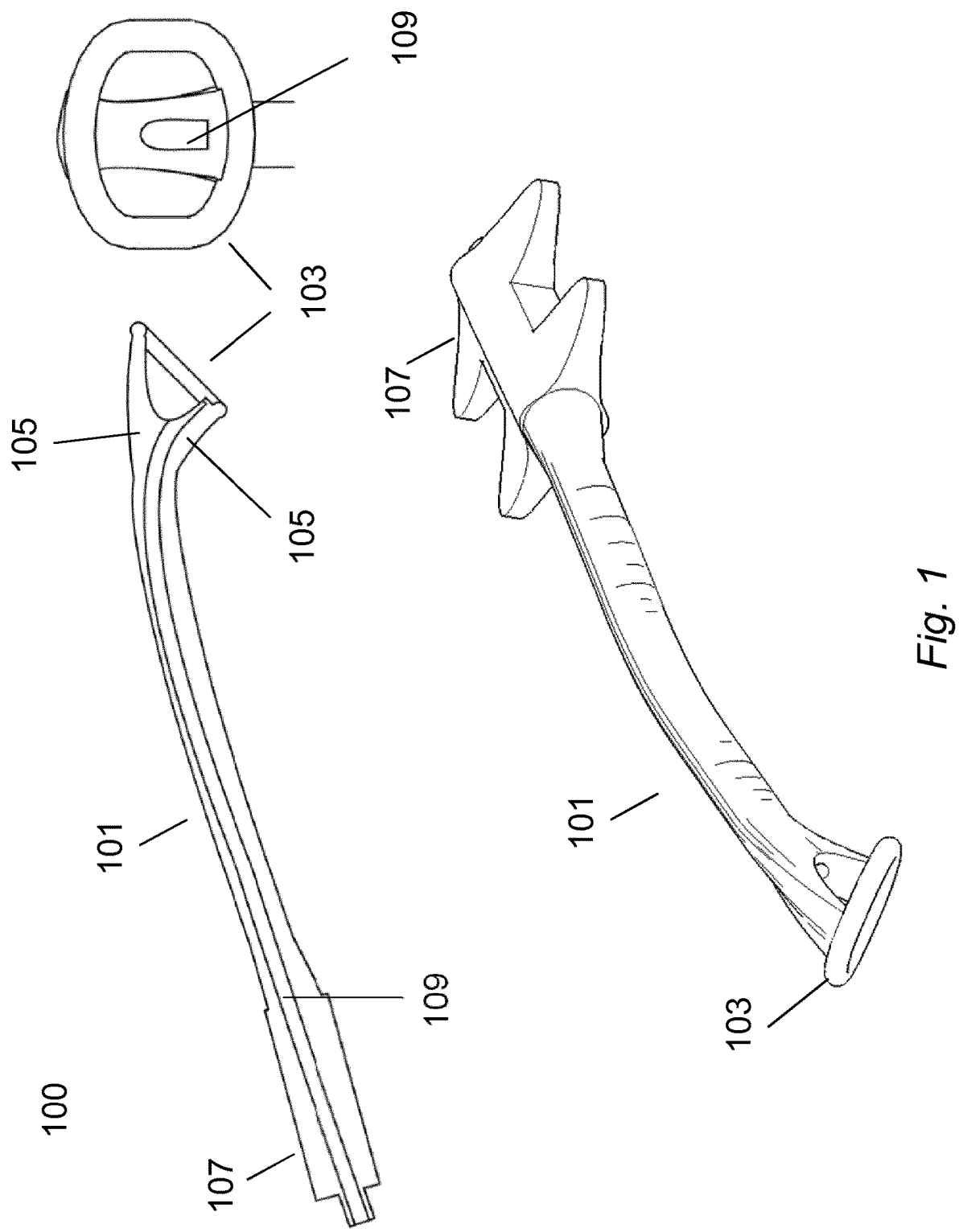
FIG. 1 show lateral and frontal view of a device implementing a particular embodiment of the present invention.

According to an embodiment of the present invention, a relatively rigid device as the one represented in FIG. 1 provides a support for positioning and for keeping in the correct place a catheter which may be used to deliver drug to the lung.

In a preferred embodiment of the present invention, device is provided with guiding means (e.g. a passing through hole) which can house a catheter for the administration of liquid or aerosol medicament.

As shown in FIG. 1 the device 100 according to the present invention comprises the following components: an elongated body (e.g. a stem) 101 for guiding and holding the catheter in the desired position and orientation; a ring-shaped element 103 attached to the stem by at least one spoke 105 for minimizing the interaction with the wall of the larynx and for creating room for the drug delivery; guiding means 109 (e.g. a passing-through hole).

Figure 2:
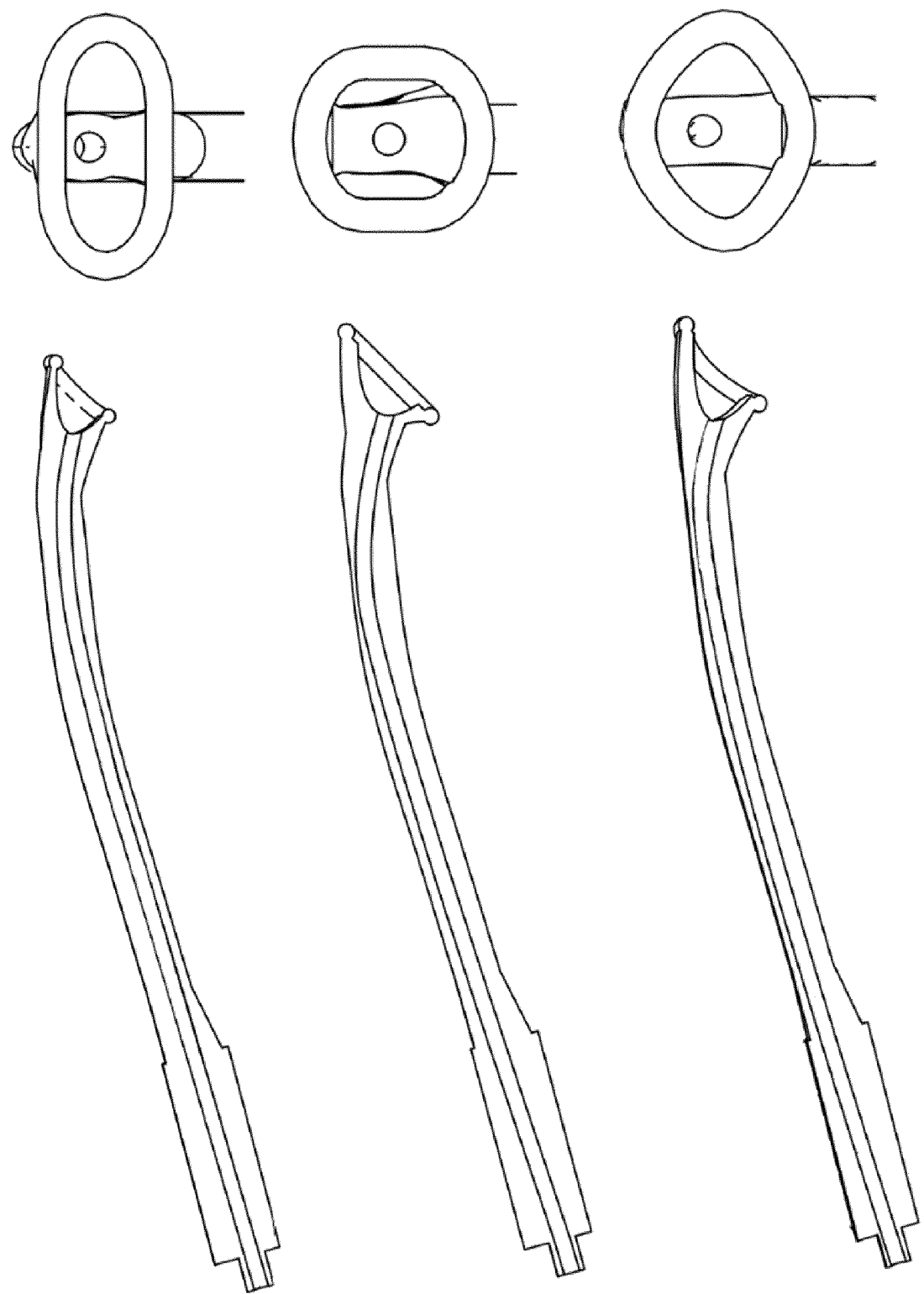
FIG. 2 shows lateral and frontal view of additional examples of devices implementing a particular embodiment of the present invention.

The shape, the dimensions and the curvature of the device can be modelled to the internal shape of the patient's throat and is adapted to arrive with its distal end in the retropharyngeal region. The final portion of the device (the distal end) shows increased dimensions and is provided with a substantially ring-shaped element which engages the walls of the pharyngeal cavity and which has the function of keeping the retro-pharynx (which is a sort of virtual place) open and of maintaining the catheter in the right position and orientation, avoiding that the catheter tip touches the walls of the retro-pharynx. FIG. 2 shows some possible alternative embodiments with different possible shapes of the stem and the ring shaped element. In a preferred embodiment of the present invention, the substantially ring-shaped element is connected to the main body of the device by means of two spokes, so that a sort of chamber is created in the immediate proximity of the exit of through hole where the tip of the catheter delivers the aerosol medicament. While in the presently described embodiment the distal end has substantially a ring shape, other solutions are not to be excluded, provided they guarantee the creation of a sort of chamber where the medicament is delivered through the catheter. The medicament is atomized in this area so that it can be carried by the inspiratory flow before hitting the airways walls. Because of the "open" structure the final part of the device does not prevent the passage of the air and the delivery of the medicament by means of the catheter can be combined with non-invasive ventilation (e.g. nasal CPAP). Accordingly to this aim, the thickness of ring-shaped element's wall should be a trade-off between to provide sufficient mechanical stability to the ring and to minimize the resistance to the breathing flow coming from the nose.

The diameter of the cross section the ring-shaped element (torus section) or the characteristic dimension if the cross section is not a circle, should range between 0.5 mm to 5 mm according to the mechanical properties of the material. Moreover, to better adjust to the patient's anatomy and to evenly distribute the contact pressure on the pharynx region walls, the ring can be provided by an inflatable element e.g. a tube (see FIG. 3). With regard to the wall of the ring-shaped element, a balance should be found between minimizing the airways resistance for spontaneous breathing and engaging the pharyngeal walls as to reduce local pressure transmitted to the wall.

Figure 3:
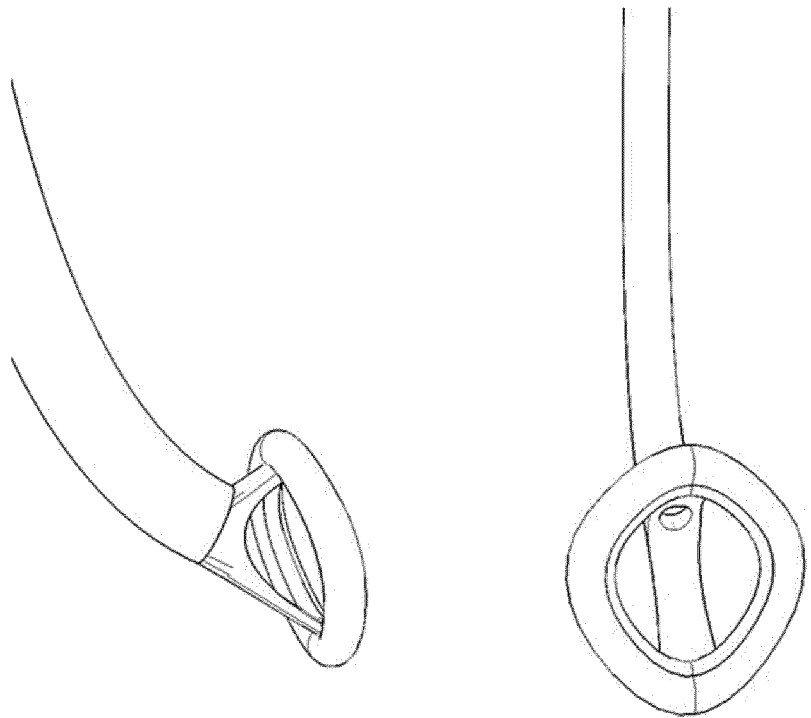
FIG. 3 shows a particular embodiment of the present invention characterized by an inflatable ring and a flexible stem.
Figure 3:
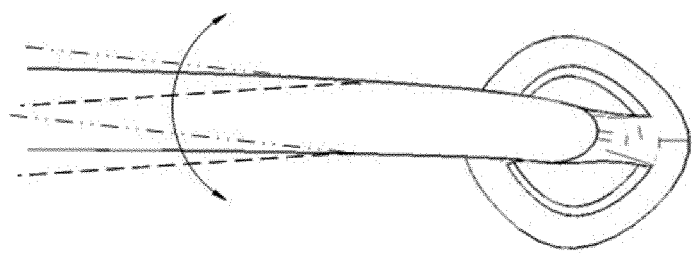

FIG. 3 shows a possible implementation for the ring shaped element. In this embodiment, the interaction with the walls of the pharynx has been reduced by using an inflatable ring. In more detail, the ring shaped element is made of two separate elements, a very thin rigid ring used to provide stability and to provide support for connection to the spokes and a second outer inflatable ring. The inflatable ring addresses two aims: 1) the reduction of the forces transmitted to the wall, by adapting to the anatomy and distributing the forces on a larger surface and 2) a better stabilization of the distal end of the device, by providing a more firm engagement with the patient's pharinx.

In this case, the presence of the inflatable ring can also be used to measure the pressure in the pharyngeal region in order to synchronize the delivery of the drug as said inflatable ring can be used as tapping point by connecting a pressure transducer to the catheter used to inflate the ring.

Figure 4:
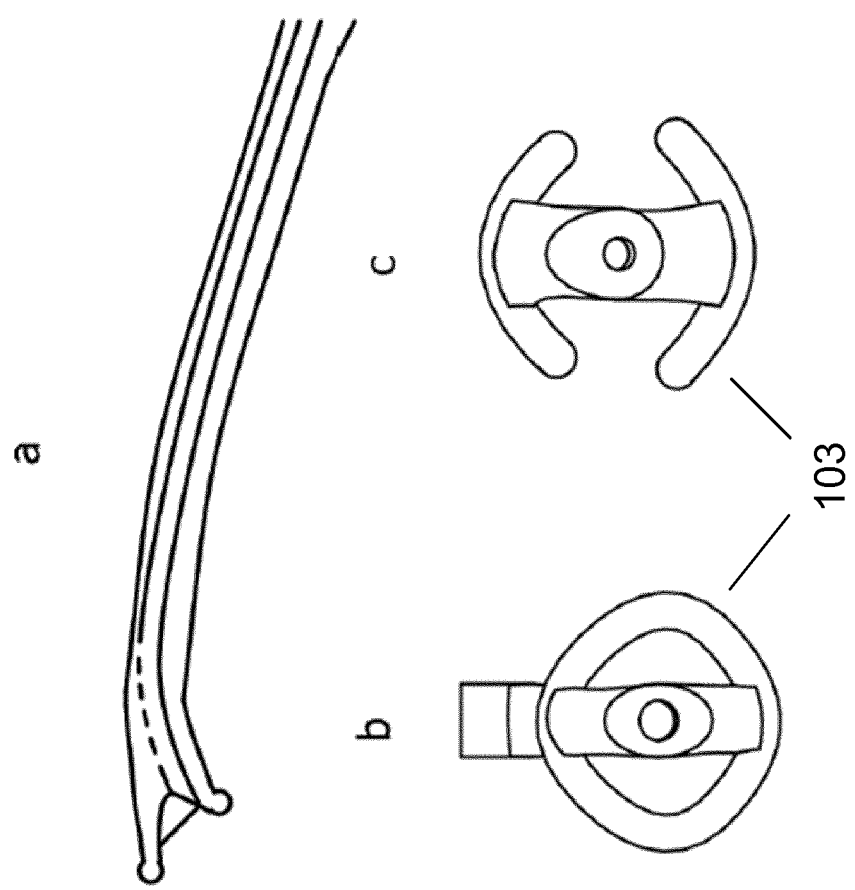
FIG. 4 shows a lateral view of a device according to an embodiment of the present invention and a front view of two possible embodiment of the substantially ring-shaped element.
Figure 5:
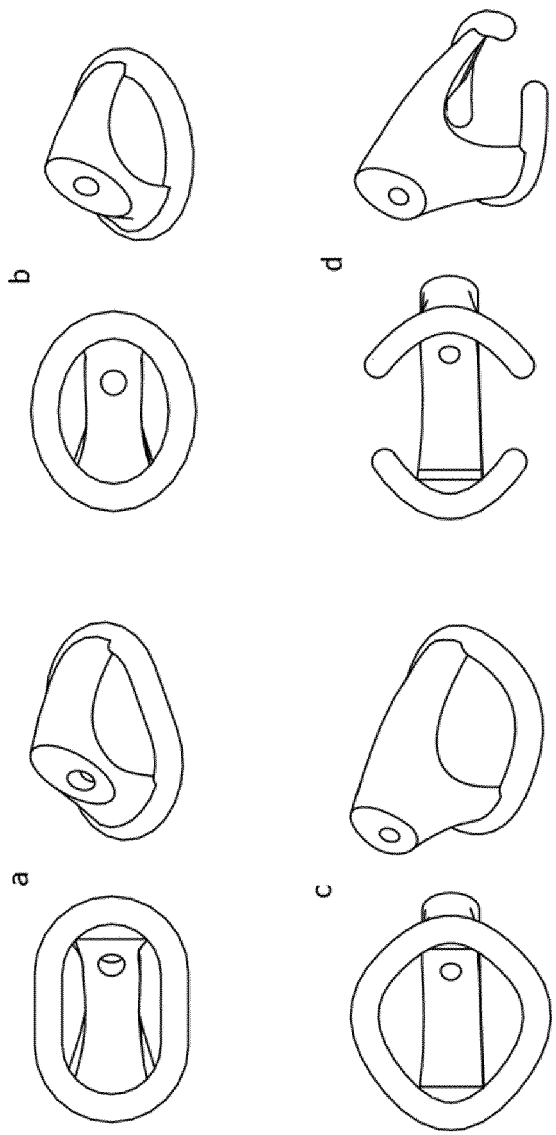
FIG. 5 shows different examples of the substantially ring-shaped element according to possible embodiment of the present invention.

Some possible alternatives of the substantially ring shaped element 103 are shown in FIGS. 4 and 5, including solutions (see e.g. FIG. 4.c and FIG. 5.d) where the substantially ring shaped is not a proper closed ring, but it is interrupted. Even this solution, which reduces resistance to respiratory airflow, should be able to minimise the interaction with the pharynx walls in order to have a better distribution of pressure on walls.

The aim of the ring-shaped element is to stabilize the last part of the interface by engaging the pharyngeal walls so to keep the relative position of the distal part of the interface integral with the inlet of the trachea unless the position of the head. The rationale to do so can be empirically verified by putting two fingers at the side of the cricoid cartilage and by moving the head left and right, although the head is moving, the fingers on the throat are not.

In a preferred embodiment, on the opposite end of the device a positioning element 107 (see FIG. 1), having the shape of a plate is provided to help fixing the device into the patient mouth and keeping the device firmly in place.

Figure 6:
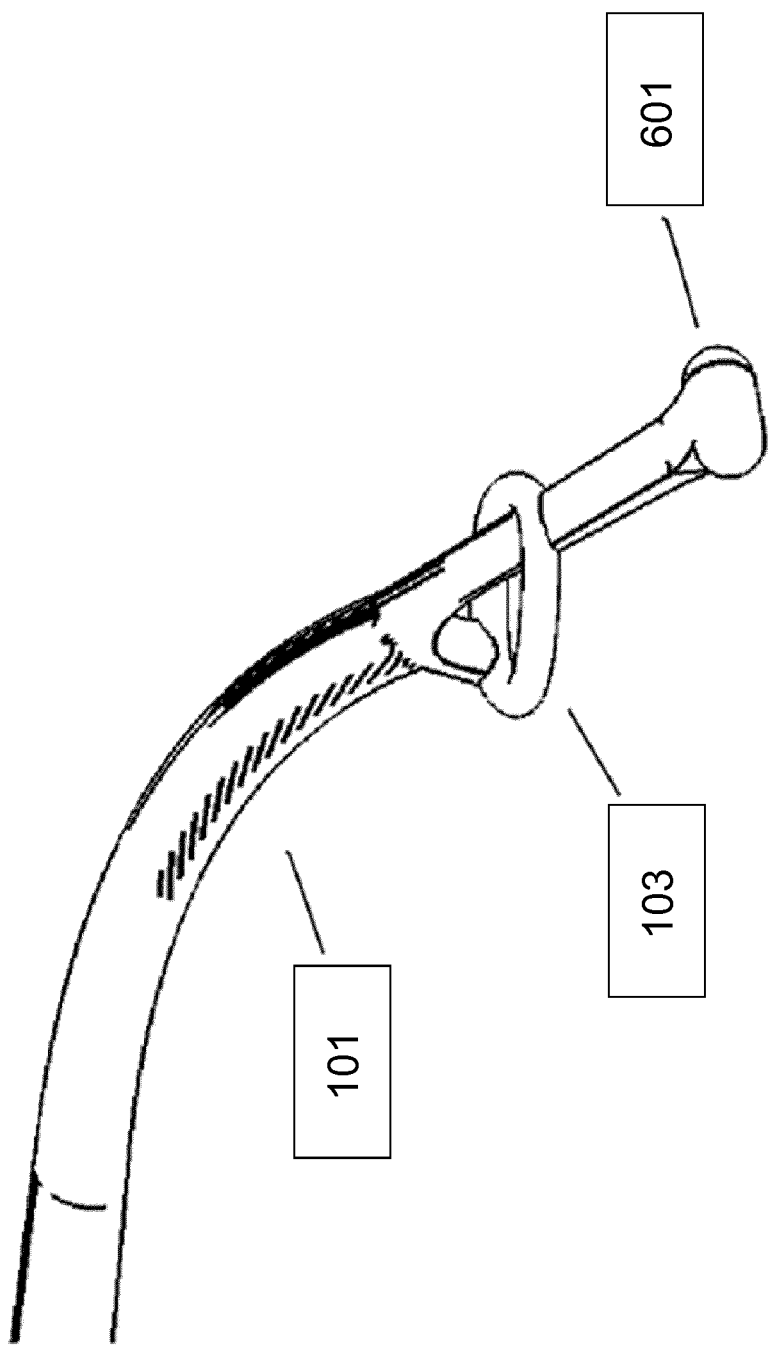
FIG. 6 shows an alternative embodiment of the present invention.

As shown in FIG. 6 the device 100 can optionally include a tip 601 extending from the stem 101 for facilitating the insertion of the device 100 into the patient's mouth.

When the tip 601 is present, the stem 101 provides the support for handling and inserting it. The stem 101 extends from the mouth of the patient to the retro-pharynx, with a shape that fits the anatomy of the upper airways of the patient. The stem 101 is intended: 1) to guide and hold an atomizing catheter conveying the medicament from the mouth to the retro-pharynx in the proper position and with a specific orientation; 2) to support the other elements of the device (the ring-shaped element 103 and the optional tip 601) and 3) to allow the handling and insertion of the system and to contribute to keep the proper position of the device 100 thanks to its shape that mimics the anatomy of the upper airways of the patient. Since the device should not impede the spontaneous nasal breathing, the stem shape could be more developed in the sagittal plane than in the lateral one (in the distal end) or at least with the same thickness in both the directions.

Accordingly, the skilled person in the art shall modify the shape of the stem in order the mimic the anatomy of the upper airway of patient.

Moreover, in order to allow a better freedom to relative movement between the ring-shaped element placed in the pharynx and the mouth (due, for example, to the rotation of the head of the patient), the stem could incorporate a section of more flexible material. In order for the device 100 to provide proper guidance to a catheter it is necessary a housing where the catheter can be inserted or positioned. Such housing can be a lumen (i.e. a passing through hole 109 as mentioned above) which can develop along the stem or, in an alternative embodiment, it can develop along a different line to 1) reduce the curvature for the catheter and to ease the insertion of the catheter and 2) provide the appropriate direction of the catheter tip.

The person skilled in the art shall select the inner diameter of the passing-through hole 109 depending on the diameter of the utilized catheter.

In a preferred embodiment of the present invention, the bending of the device should follow the shape on the patient's throat, in particular the orientation of the catheter should address the medicament in the patient's lungs; in fact if the catheter is not properly positioned, the medicament (e.g. a surfactant) might not properly enter the respiratory system. Anyway, thanks to the stabilization effect of the distal end of the device provided by the ring shaped element, a precise mimicking is not needed.

In a preferred embodiment, the shape of the device, in particular the shape of the substantially ring-shaped element, helps in the positioning of the device itself within the patient's larynx: it should be avoided that the device could be pushed too far down the larynx, otherwise it would stimulate lot of reflexes that induce a laryngo-spasms glottis closure, alteration of normal breathing pattern (e.g. reduction of respiratory rate).

On the other hand, if the device is not down enough the medicament (e.g. a surfactant) deposits on the pharynx walls and it is swallowed by the patient.

Also it should be considered that the area where the device enters into contact with the patient is very sensitive.

In a preferred embodiment of the present invention, the device should have dimensions determined by the anatomy, in particular considering the example of a human pre-term neonate as a patient: 1) part of the stem extends from the mouth to the retro pharynx, so the length of this part can be from 40 to 60 mm, depending on the weight of the patient, 2) the part of the stem outside the mouth is from 30 to 70 mm long, it is used to keep in place the catheter and to make easier the handling, 3) the curvature radius is from 10 to 30 mm according to the weight of the pre-term neonate and 4) the ring a maximum radius of 7.5 mm with a cross section of the torus ranging from 0.5 to 5 mm.

When the device of the present invention is used in combination with a catheter mounted on an atomizing device, the stem will also provide a correct placement for said atomizing catheter, whose distal tip should be few millimeters above the vocal chords, and a proper direction of the atomizing tip, as it should point towards the trachea and not towards the esophagus or laryngeal/pharyngeal walls.

The cross section of the stem can be an ellipse or any rounded smoothed shape (see FIGS. 4 and 5) with the external dimensions as small as possible in order to avoid hurting the soft tissues of the airways and in order to decrease the resistance opposed to the air flow.

As shown in FIG. 3, according to another possible embodiment, the stem can be also made of three parts: the distal one made of rigid plastic to orientate the atomizing catheter towards the inlet of the trachea, the central part can be made of a softer material which can adapt to the anatomy improving tolerability and comfort for the patient, and the proximal end made of rigid material to help the operator in deploying the catheter.

The stem can be manufactured with material such as for example: polyethylene (PE), polyvinyl chloride (PVC), polyurethane (PU) or medical grade silicone.

If the interface is used in conjunction with a system such as the atomizing catheter that delivers a certain amount of airflow to the patient, it is possible to carve in the stem additional lumens that can provide a path through the atmosphere to the exceeding gas, providing an intrinsic safe system to avoid the development of over pressure into the pharynx.

The ring-shaped element 103 is attached to the stem by small spokes 105 and it surrounds the tip of the catheter. It is positioned in order to keep the collapsible walls of the retro-pharynx far enough from the tip of the catheter.

The substantially ring-shaped element can be made of the same material of the stem or with a softer material, for example medical grade silicone and designed with a rounded section to facilitate the insertion of the device 100 and to minimize the interaction with the wall of the larynx to prevent possible reflexes that may induce a laryngo-spasms, glottis closure or alteration of the breathing pattern (e.g. reduction of respiratory rate).

In a preferred embodiment the ring-shaped element is connected to the stem by means of two spokes in the upper and lower part. However other alternative arrangements are possible, e.g. there can be only one spoke, or more than two spokes and they could be differently positioned, e.g. they can be on the sides. One of the advantages of the device according to the present invention is that the passage of the air is not prevented by the shape of the device, therefore any number and shape of the spoke which allows the passage of air can be an acceptable alternative. The substantially ring-shaped element may assume different shapes as shown in FIG. 5, which are designed to better fit slightly differences in the anatomy. It can be a proper ring or a partial substantially ring-shaped element.

In particular FIG. 5.d shows an example of open ring that can be used to reduce the contact with the pharynx. The orientation of the plane of the ring (or the virtual ring in case of configurations with not complete rings) compared to the stem should be driven by the anatomy to allow the ring would be properly pointed toward the trachea.

Accordingly the skilled person in the art shall adapt the orientation of the plane of the ring compared to the stem depending on the anatomy of the patient.

The optional tip 601 is the very distal end of the device and it is an extension of the stem enlarging beyond the ring (see FIG. 6). When present, the optional tip 601 allows 1) an easy insertion of the device of the invention in the pharynx through the mouth and 2) it is intended to help self-positioning of device, by allowing the identification of the lower end of the pharynx, at the entrance of the esophagus.

Figure 7:
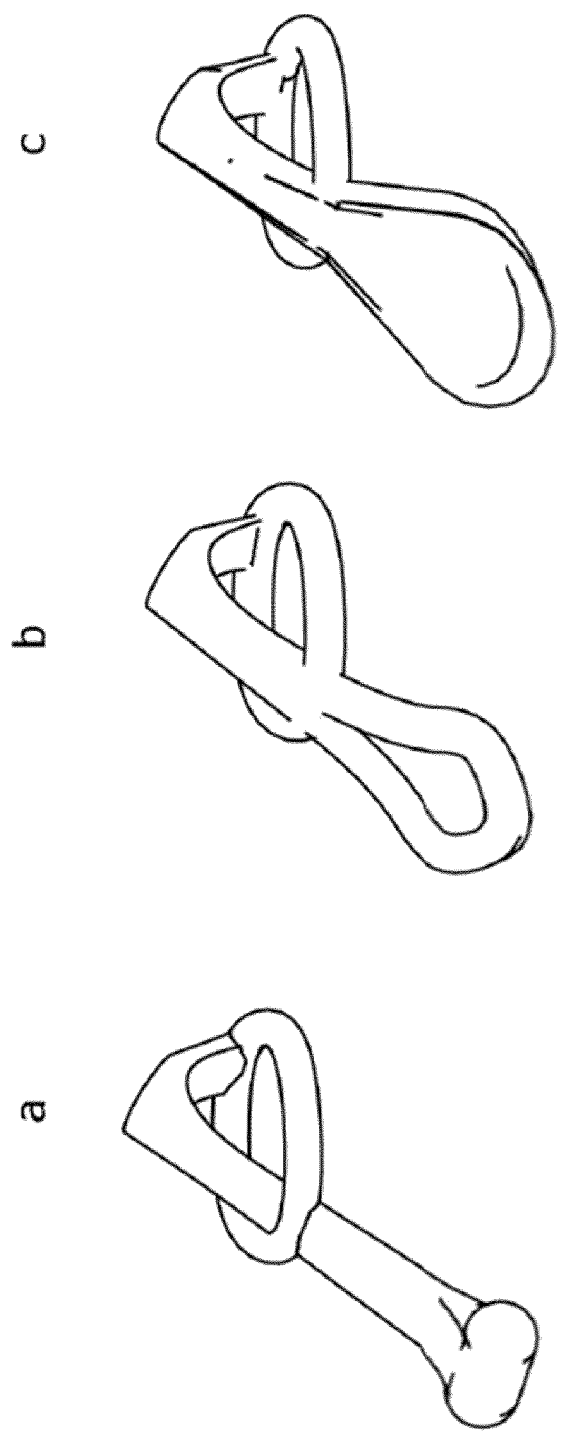
FIG. 7 shows possible examples of the optional tip.

In fact, when the tip reaches this position it makes it harder to further advance it, preventing the device of the invention to be inserted too deep. In particular, the shape of the tip should be designed to be too large to be easily inserted into the esophagus. For this reason, it is recommended a shape characterized by an increase in lateral dimension, for example the shape of a sphere (see FIG. 7.a), of a ring (FIG. 7.b) or of a nose cone (FIG. 7.c) maximizing the quantity of drug delivery to the lung.

Figure 8:
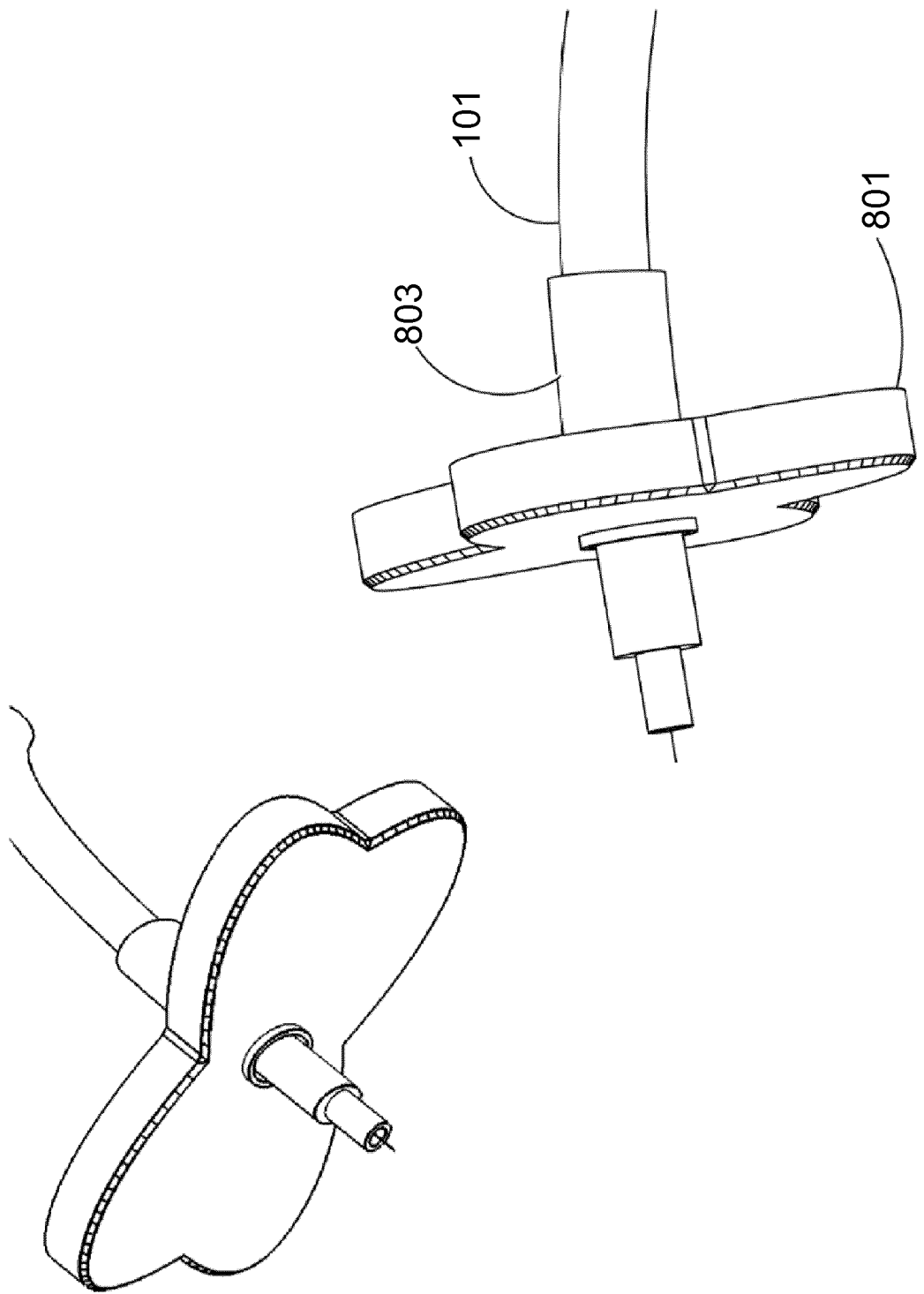
FIG. 8 shows an example of the optional positioning element according to an embodiment of the present invention.

Optionally, another component of the device is made of a plate (801) connected to the stem through a connector allowing changes in the length of the part of the stem between the plate and the tip of the device as shown in FIG. 8. This plate can also be provided by a soft short elastic tube (803) surrounding the first part of the stem, which mimics a pacifier. The plate is kept out of the mouth and helps in maintaining the whole device in the proper position limiting the leaks from the mouth facilitating the maintenance of a close-mouth condition during administration of the treatment. This latter condition is desirable because 1) it is more physiological, 2) it allows the delivery of a constant known pressure during CPAP therapy and 3) it maximizes the pressure swings at the pharynx, improving, therefore, the efficiency of the systems to identify the phase of the breath to synchronize the delivery of the treatment during inspiration only.

In a preferred embodiment, the positioning device can move along the stem in order to be placed in the right position depending on the size of the baby and it is made of soft material such as medical grade silicone.

In the present application we addressed the problem of delivering the right amount of atomized medicament to a patient, e.g. a preterm neonate. In a preferred embodiment, the medicament is a pulmonary surfactant, e.g. an exogenous pulmonary surfactant.

In this respect, any pulmonary surfactant currently in use, or hereafter developed for the prophylaxis and/or treatment of Respiratory Distress Syndrome (RDS) or other pulmonary conditions related to the deficiency of endogenous pulmonary surfactant could be suitable for use in the present invention. These include modified natural, artificial and reconstituted pulmonary surfactants (PS).

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf®, Chiesi Farmaceutici SpA, Parma, Italy), and beractant (Survanta™, Abbott Laboratories, Inc., Abbott Park, Ill.)

Examples of artificial surfactants include, but are not limited to, pumactant (Alec™' Britannia Pharmaceuticals, UK), and colfosceril palmitate (Exosurf™, GlaxoSmithKline, plc, Middlesex).

Examples of reconstituted surfactants include, but are not limited to, lucinactant (Surfaxin™, Discovery Laboratories, Inc., Warrington, Pa.) and the product having the composition disclosed in Table 2 of Example 2 of WO 2010/139442, whose teaching is incorporated herein by reference.

Advantageously, the pulmonary surfactant is a modified natural surfactant or a reconstituted surfactant. More preferably the pulmonary surfactant is poractant alfa (Curosurr). In another preferred embodiment, the reconstituted surfactant has composition disclosed in WO 2010/139442 (see Table 2 of Example 2).

Preferably, the pulmonary surfactant is administered as a suspension in a sterile pharmaceutically acceptable aqueous medium, preferably in a buffered physiological saline (0.9% w/v sodium chloride) aqueous solution.

Its concentration shall be properly adjusted by the skilled person in the art. Advantageously, the concentration of the surfactant might be comprised between 2 and 160 mg/ml, preferably between 10 and 100 mg/ml, more preferably between 40 and 80 mg/ml.

The dose of the pulmonary surfactant to be administered varies with the size and age of the patient, as well as with the severity of the patient's condition. Those of skill in the relevant art will be readily able to determine these factors and to adjust the dosage accordingly.

Other active ingredients that could advantageously be comprised in the medicament according to the invention include those currently used for the prevention and/or treatment of neonatal respiratory diseases, for example inhaled corticosteroids such as beclometasone dipropionate and budesonide.

The present invention also concerns the use of the device herein disclosed in combination with a catheter for the delivery of a medicament to spontaneously breathing patients.

In a particular embodiment, a catheter for minimally invasive endotracheal administration of a pulmonary surfactant could be utilized, for example according to procedure disclosed in WO 2008/148469 or in Dargaville P A et al Arch Dis Fetal Neonatal Ed 2013, 98(2), 122-126. Said catheter should have a diameter equal to or lower than 5 French (hereinafter Fr) corresponding to about 1.66 mm (1 French corresponds to ⅓ mm). Advantageously the diameter shall be comprised between 2.0 and 5.0 Fr. Preferred diameters would be 3.5, 4.0 and 5.0 Fr.

To act as a catheter according to the invention, any gastric or nasogastric tube, arterial or suction catheter of common use in hospitals can be utilized. It may be made of any material, preferably of polyurethane or silicone, and could have a length comprised from 10 to 35 cm, preferably of 15 cm or 30 cm.

In another particular embodiment, the catheter is mounted on a system for delivering by atomization a medicament in the retro- or pharyngeal region such as that disclosed in WO 2013/160129. Preferably, the delivery of the atomized medicament is done by means of an air blasting technique. Using air to assist atomization is a well-known technique that grants a fully developed atomization also when low pressure and low flow conditions are required (see e.g. Arthur Lefebvre, "Atomization and spray", Taylor and Francis, 1989). Such technique is based on a relatively small amount of gas (e.g. air, but it could be other compressed gas, e.g. oxygen, nitrogen, or helium) which flows in one or more separate channels than the medicament which is delivered in a liquid form; the air flow accelerates and breaks the liquid column, inducing the atomization of the medicament. Therefore the multi-lumen catheter includes a plurality of channels (at least two, one for the medicament and one for the air) for conveying contemporarily the medicament and the air flow. The liquid medicament column is broken up in droplets by the turbulence due to the air flowing next or around when the two flows (air and liquid medicament) exit the catheter channels and meet in the retro-pharyngeal region. The atomized droplets have a median diameter of at least 20 micron, preferably equal to or higher than 40 micron, more preferably equal to or higher than 60 micron. It is believed that this effect is caused by the air flow which accelerates the fluid sheet instability. The air also helps in dispersing the droplets, preventing collision among them and facilitating the diffusion of the medicament in the lungs by reducing the likelihood of contact between the particles and the wall of the retropharyngeal cavity.

In a preferred embodiment, the multi-lumen catheter could present a length of 7-15 cm and an internal diameter of 0.6-0.8 mm. According to a more preferred embodiment the lumen through which the medicament passes has a diameter of 0.75 mm, while the lateral lumen for gas may be a single lumen for all the length of the catheter except for the 5 distal millimetres at the tip, where it can change its shape into a plurality of lumens coaxial to the surfactant lumen.

Alternatively, the multi-lumen catheter disclosed in the co-pending application EP 13189768.8 whose teaching is incorporated herein by reference, could be utilized. In a preferred embodiment of the invention, the device herein disclosed is used in combination with a multi-lumen catheter conveying the atomized medicament (e.g. a pulmonary surfactant) directly to the retro-pharyngeal region in order to increase efficiency of the medicament administration without being invasive: this is particularly important for very young patients, such as pre-term neonates suffering from neonatal Respiratory Distress Syndrome (nRDS).

In order to deliver a nebulized drug to the lung, other strategies than air blasting catheter could be used with the present invention. For example, piezoelectric devices such as vibrating mesh nebulizers or a SAW (surface acoustic waves) nebulizer such as that disclosed in WO 2014/13228 could be fitted into the distal part of the main lumen of the stem in place of the tip of the air blasting catheter.

Advantageously, the device of the invention is used for administering a medicament through a catheter to any spontaneously breathing patient, more advantageously to a spontaneously breathing human neonate, preferably to pre-term neonate. In a particular embodiment, the device of the invention is used for administering a medicament through a catheter to pre-term very-low-birth-weight-neonates of 24-35 weeks gestational age that are spontaneously breathing, and demonstrate early signs of respiratory distress syndrome as indicated either by clinical signs and/or supplemental oxygen demand (fraction of inspired oxygen ($FiO_2$) >30%). In a further aspect of the invention, a method for preventing and/or treating a respiratory distress syndrome in a spontaneously breathing patient is provided, said method comprising applying the device herein disclosed in combination with a catheter a for the delivery of a medicament. However, the therapeutic method could also be intended for the prevention and/or treatment of any disease related to a surfactant-deficiency or dysfunction as well as of conditions in which respiratory distress may be present that include, but are not limited to, meconium aspiration and pulmonary infection. Preferably, the method of the invention comprises applying to the patient a non-invasive ventilation procedure such as nasal Continuous Positive Airway Pressure (nCPAP).

Advantageously, nasal Continuous Positive Airway Pressure (nCPAP) is applied to said patients, according to procedures known to the person skilled in the art.

Preferably a nasal mask or nasal prongs are utilised. Any nasal mask commercially available may be used, for example those provided by The CPAP Store LLC, and the CPAP Company.

Nasal CPAP is typically applied at a pressure comprised between 1 and 12 cm H2O, preferably 2 and 8 cm H2O, although the pressure can vary depending on the neonate age and the pulmonary condition.

Other non-invasive ventilation procedures such as nasal intermittent positive-pressure ventilation (NIPPV), bi-level positive airway pressure (BiPAP) or high flow nasal cannula (HFNC) could alternatively be applied to the patients.

It will be appreciated that alterations and modifications may be made to the above without departing from the scope of the disclosure. Naturally, in order to satisfy local and specific requirements, a person skilled in the art may apply to the solution described above many modifications and alterations. Particularly, although the present disclosure has been described with a deep degree of particularity with reference to preferred embodiment(s) thereof, it should be understood that eventual omissions, substitutions and changes in the form and details as well as other embodiments are possible; moreover, it is expressly intended that specific elements and/or method steps described in connection with any disclosed embodiment of the disclosure may be incorporated in any other embodiment as a general matter of design choice.

The invention claimed is:

1. A device specifically adapted to position a catheter for the delivery of a liquid medicament in the form of a liquid pulmonary surfactant to the lungs of a spontaneously breathing patient, the device comprising:
    an elongated main body shaped to follow an internal shape of the patient's upper airways, the elongated main body being provided with an internal channel adapted to house the catheter;
    a substantially ring-shaped terminal element adapted to engage an internal wall of the spontaneously breathing patient's retro-pharynx, the substantially ring-shaped terminal element being connected to a distal end of the elongated main body by a plurality of spokes, the substantially ring-shaped terminal element and the plurality of spokes creating a chamber to receive delivery of the liquid pulmonary surfactant through the internal channel of the elongated main body, without impeding airflow through the spontaneously breathing patient's upper airways by way of one or more voids formed by the substantially ring-shaped terminal element and the plurality of spokes connecting the substantially ring-shaped terminal element to the distal end of the elongated main body; and
    positioning means for fixing the device to the spontaneously breathing patient,
    wherein the substantially ring-shaped terminal element has a widest part at a distal end of the device, the widest part of the substantially ring-shaped terminal element is wider than any portion of the elongated main body, the substantially ring-shaped terminal element is made of a material softer than the elongated main body, and the substantially ring-shaped terminal element includes an inflatable toroidal element ensuring the airflow through the spontaneously breathing patient's upper ways, and
    wherein the positioning means include a substantially plate shaped element.

2. The device of claim 1, wherein the inflatable toroidal element is spaced apart from and connected to the elongated main body by the plurality of spokes.

3. The device of claim 1, wherein the inflatable toroidal element has a diameter between 0.5 and 5 mm.

4. The device of claim 1, wherein a material of the elongated main body is selected from the group consisting of polyethylene (PET), polyvinyl chloride (PVC), and polyurethane (PU).

5. The device of claim 1, wherein a material of the substantially ring shaped terminal element is selected from the group consisting of polyethylene (PET), polyvinyl chloride (PVC), polyurethane (PU), and medical-grade silicone.

6. The device of claim 1, wherein the substantially ring-shaped terminal element has an elliptic shape.

7. The device of claim 1, wherein the substantially ring-shaped terminal element includes two separate portions creating a non-continuous ring adapted for reducing contact with the spontaneously breathing patient's retro-pharynx.

8. The device of claim 1, wherein the internal channel of the elongated main body defines an opening at the distal end of the elongated main body that leads directly to the chamber.

9. The device of claim 8, wherein the internal channel has a diameter of 0.5 mm to 3 mm.

10. The device of claim 1, wherein the elongated main body is flexible.

11. The device of claim 1, wherein the positioning means is disposed on a second distal end of the elongated main body, the second distal end being opposite to the distal end.

12. A system for delivering a liquid pulmonary surfactant to a patient by a catheter specifically adapted to be positioned in the patient to deliver the liquid pulmonary surfactant to the lungs of a patient, wherein the system includes:
    an elongated main body shaped to follow an internal shape of the patient's upper airways, the elongated main body being provided with an internal channel adapted to house the catheter;
    a substantially ring-shaped terminal element adapted to engage an internal wall of the patient's retro-pharynx, the substantially ring-shaped terminal element being connected to a distal end of the elongated main body by at least one spoke, the substantially ring-shaped terminal element and the at least one spoke creating a chamber to receive delivery of the liquid pulmonary surfactant through the internal channel of the catheter, without impeding airflow through the patient's upper airways by way of one or more voids formed by the substantially ring-shaped terminal element and the at least one spoke connecting the substantially ring-shaped terminal element to the distal end of the elongated main body; and
    positioning means for fixing the system to the spontaneously breathing patient,
    wherein the substantially ring-shaped terminal element defines a second opening spaced from and at least partially aligned with a first opening of the internal channel at the distal end of the elongated main body, the second opening of the substantially ring-shaped terminal element has an inner diameter greater than an inner diameter of the first opening of the internal channel, the substantially ring-shaped terminal element is made of a material softer than the elongated main body, and the substantially ring-shaped terminal element includes an inflatable toroidal element ensuring the airflow through the spontaneously breathing patient's upper ways, and
    wherein the positioning means include a substantially plate shaped element.

13. The system according to claim 12, wherein the liquid pulmonary surfactant is selected from the group consisting of modified natural pulmonary surfactants, artificial surfactants, and reconstituted surfactants.

14. The system according to any claim 12, wherein the patient is a spontaneously breathing pre-term neonate.

15. A method comprising:
    positioning a catheter for the delivery of a liquid pulmonary surfactant to the lungs of a patient, with a device specifically adapted to facilitate positioning of the catheter for the delivery of the liquid pulmonary surfactant to the lungs of the patient, the device including:
    an elongated main body shaped to follow an internal shape of the patient's upper airways, the elongated main body being provided with an internal channel adapted to house the catheter;
    a substantially ring-shaped terminal element adapted to engage an internal wall of the patient's retro-pharynx, the substantially ring-shaped terminal element being connected to a distal end of the elongated main body by at least one spoke, the substantially ring-shaped terminal element and the at least one spoke creating a chamber to receive delivery of the liquid pulmonary surfactant through the internal channel of the elongated main body, without impeding airflow through the patient's upper airways by way of one or more voids formed by the substantially ring-shaped terminal element and the at least one spoke connecting the substantially ring-shaped terminal element to the distal end of the elongated main body; and positioning means for fixing the device to the spontaneously breathing patient, wherein the substantially ring-shaped terminal element defines a second opening spaced from and at least partially aligned with a first opening of the internal channel at the distal end of the elongated main body that leads directly to the chamber, the second opening of the substantially ring-shaped terminal element has an inner circumference greater than an inner circumference of the first opening of the internal channel, the substantially ring-shaped terminal element is made of a material softer than the elongated main body, and the substantially ring-shaped terminal element includes an inflatable toroidal element ensuring the airflow through the spontaneously breathing patient's upper ways, and wherein the positioning means include a substantially plate shaped element.

16. A kit comprising:
a) a pharmaceutical composition comprising a medicament in the form of a liquid pulmonary surfactant;
b) a device configured to facilitate the introduction and positioning of a flexible catheter into the retro-pharyngeal region of a patient to deliver the liquid pulmonary surfactant to the lungs of the patient, the device including:

an elongated main body shaped to follow an internal shape of the patient's upper airways, the elongated main body being provided with an internal channel adapted to house the flexible catheter;
a substantially ring-shaped terminal element adapted to engage an internal wall of the patient's retro-pharynx, the substantially ring-shaped terminal element being connected to a distal end of the elongated main body by at least one spoke, the substantially ring-shaped terminal element and the at least one spoke creating a chamber to receive delivery of the liquid pulmonary surfactant through the elongated main body, without impeding airflow through the patient's upper airways by way of one or more voids formed by the substantially ring-shaped terminal element and the at least one spoke connecting the substantially ring-shaped terminal element to the distal end of the elongated main body; and
positioning means for fixing the device to the spontaneously breathing patient; and
c) a container configured to contain the liquid pulmonary surfactant, the flexible catheter, and the device,
wherein the substantially ring-shaped terminal element has a widest part at a distal end of the device, the widest part of the substantially ring-shaped terminal element is wider than any portion of the elongated main body, the substantially ring-shaped terminal element is made of a material softer than the elongated main body, and the substantially ring-shaped terminal element includes an inflatable toroidal element ensuring the airflow through the spontaneously breathing patient's upper ways, and
wherein the positioning means include a substantially plate shaped element.

* * * * *